United States Patent
Cinquin et al.

(10) Patent No.: US 11,660,314 B2
(45) Date of Patent: May 30, 2023

(54) IMPLANTABLE DEVICE FOR PRODUCING HYDROGEN

(71) Applicants: UNIVERSITE GRENOBLE ALPES, Saint Martin d'Heres (FR); CENTRE HOSPITALIER UNIVERSITAIRE GRENOBLE ALPES, La Tronche (FR); INSTITUT NATIONAL DE LA SANTE ET DE LA RECHERCHE MEDICALE (INSERM), Paris (FR)

(72) Inventors: Philippe Cinquin, Saint Nazaire les Eymes (FR); Abdelkader Zebda, Grenoble (FR); Jean-Pierre Alcaraz, Pontcharra (FR); Donald Keith Martin, Gieres (FR)

(73) Assignees: UNIVERSITE GRENOBLE ALPES, Saint Martin d'Heres (FR); CENTRE HOSPITALIER UNIVERSITAIRE GRENOBLE ALPES, La Tronche (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 261 days.

(21) Appl. No.: 16/956,842

(22) PCT Filed: Dec. 21, 2018

(86) PCT No.: PCT/EP2018/086811
§ 371 (c)(1),
(2) Date: Aug. 25, 2020

(87) PCT Pub. No.: WO2019/122441
PCT Pub. Date: Jun. 27, 2019

(65) Prior Publication Data
US 2020/0390802 A1     Dec. 17, 2020

(30) Foreign Application Priority Data

Dec. 22, 2017 (FR) .................................... 1763088

(51) Int. Cl.
*A61K 33/00* (2006.01)
*A61K 9/00* (2006.01)
(Continued)

(52) U.S. Cl.
CPC ............ *A61K 33/00* (2013.01); *A61K 9/0024* (2013.01); *A61N 1/05* (2013.01); *A61N 1/32* (2013.01)

(58) Field of Classification Search
CPC ........ A61K 33/00; A61K 9/0024; A61N 1/05; A61N 1/32; C25B 1/04; C25B 9/19;
(Continued)

(56) References Cited

U.S. PATENT DOCUMENTS 6,368,592 B1   4/2002  Colton et al.
6,503,648 B1   1/2003  Wang
(Continued)

FOREIGN PATENT DOCUMENTS

EP   2375481 A1   10/2011
FR   2930076 A1   10/2009
FR   3034307 A1   10/2016

OTHER PUBLICATIONS

International Search Report from corresponding International Application No. PCT/EP2018/086811, dated Apr. 9, 2019, pp. 1-3, European Patent Office, Rijswijk, The Netherlands.
(Continued)

*Primary Examiner* — Mark W. Bockelman
(74) *Attorney, Agent, or Firm* — Hauptman Ham, LLP

(57) ABSTRACT

A device intended to be implanted in a human or animal body, in order to produce hydrogen in situ from molecules
(Continued)

present in the body medium in which the device is implanted, this device having an anode and a cathode, which are each electrically connected to a pole of an electrical energy source, and having a semi-permeable material separating the electrodes from the body medium, in which device, when the connection to the electrical energy source is effective in situ, in the presence of body fluid, a closed electrical circuit is formed, with production of hydrogen at the cathode, the semi-permeable material having a cutoff threshold of between 50 and 500 Da.

19 Claims, 3 Drawing Sheets

(51) Int. Cl.
*A61N 1/05* (2006.01)
*A61N 1/32* (2006.01)

(58) Field of Classification Search
CPC .. C25B 9/00; C25B 9/73; C25B 15/08; Y02E 60/36
See application file for complete search history.

(56) References Cited

U.S. PATENT DOCUMENTS

| | | |
|---|---|---|
| 9,005,187 B2 | 4/2015 | Ziaie et al. |
| 2005/0136092 A1 | 6/2005 | Rotem et al. |
| 2015/0112247 A1 | 4/2015 | Tempelman et al. |
| 2017/0105832 A1 | 4/2017 | Rosenblum |

OTHER PUBLICATIONS

Written Opinion from corresponding International Application No. PCT/EP2018/086811, pp. 1-6, European Patent Office, Munich, Germany.

IMPLANTABLE DEVICE FOR PRODUCING HYDROGEN

RELATED APPLICATIONS

The present application is a U.S. National Phase of International Application Number PCT/EP2018/086811, filed Dec. 21, 2018, and claims the priority of French Application No. 1763088, filed Dec. 22, 2017.

DOMAIN OF THE INVENTION

The present invention relates to a device that can be implanted in a human or animal body, intended to produce hydrogen and optionally oxygen.

TECHNOLOGICAL BACKGROUND

Shigeao Ohta (Pharmacology & Therapeutics 144, 2014, 1-11) describes the medical interest of molecular hydrogen. The methods for ingesting hydrogen include inhalation of gas, oral ingestion of water or of a saline solution containing dissolved hydrogen or the incorporation of molecular hydrogen by diffusion from eye drops, baths and cosmetics.

Local production of $O_2$ can also be of interest for the areas of the organism that are insufficiently oxygenated. In normal physiological conditions, the partial pressure in $O_2$ in venous blood can be estimated at 50 micromoles/L. This is therefore also the partial pressure observed in the extracellular fluid in the vicinity of the capillary network. However, in certain circumstances, certain tissues can be momentarily or definitively excluded from the supply of $O_2$ by the vessels.

In using hydrogen and oxygen for therapeutic or physiological purposes, one of the difficulties encountered is the method for delivering and for supplying these molecules.

An objective of the invention is to propose a device making it possible to produce $H_2$ and/or $O_2$ in situ.

Another objective of the invention is to propose such a device making it possible to produce these molecules as close as possible to the site where these molecules are used, for example organ, cavity, tissue.

SUMMARY

The present invention thus has for object a device intended to be implanted in a human or animal body, in order to produce hydrogen and/or oxygen in situ, from molecules present in the body medium in which the device is implanted. In an embodiment, the device aims to produce and to deliver hydrogen in situ. In an embodiment, the device aims to produce and to deliver oxygen in situ. In another embodiment, the device aims to produce both. The device includes an integrated electrical energy source, or is intended to be connected to an electrical energy source exterior to the device and preferably integrated into the body. The device includes at least one group of electrodes, wherein the electrodes of one group are electrically connected to the electrical energy source in such a way as to form an anode and a cathode. The electrodes are separated from the external environment (the body medium in which the device is implanted) by a semi-permeable material (also referred to as filtering material). The cathode is able to produce hydrogen by proton reduction. The anode is able to produce oxygen or oxidation products (gluconic acid, for example), according to the chemical species available at the anode and according to the level of the difference in potential between the anode and cathode (at least 1.3 V is required to hydrolyse $H_2O$, but in the presence of the enzyme glucose oxidase and a redox mediator, at voltages of about 300 mV, the glucose can be oxidised effectively at the anode and the protons can be reduced at the cathode.). As shall be explained in the rest of the disclosure, the cutoff threshold of the semi-permeable material can be chosen to select the molecules that are desired to be presented at the anode and/or at the cathode, so as to favour the desired reactions and prevent pollution that generates secondary reactions that can create chemical species that are potentially harmful for the body or able to be deposited on the electrodes and decrease their performance. The semi-permeable material can in particular be a piece of solid material, a membrane, flexible by nature, or a covering on the electrode (coating).

The invention has in particular for object a device that includes two electrodes, namely an anode and a cathode, which are each electrically connected to a pole of an electrical energy source. This connection is carried out preferably by an insulated conductor. Anode and cathode are separated by an ionic conductor (liquid comprising electrolytes or ion-conducting membrane, more preferably associated with a liquid comprising electrolytes). The device further comprises a semi-permeable material (or filtering) separating the electrodes from the body medium. Advantageously, the device allows a body liquid to pass that will form the electrolyte, making it possible to close the electrical circuit. When the connection to the electrical energy source is effective, a closed electrical circuit is formed. Oxidation and reduction reactions are obtained at the electrodes. The cathode is able to produce hydrogen by proton reduction.

Thus, the invention has for object a device intended to be implanted in a human or animal body, in order to produce hydrogen in situ from molecules present in the body medium in which the device is implanted, this device having an anode and a cathode, which are each electrically connected to a pole of an electrical energy source, and having a semi-permeable material separating the electrodes from the body medium, in which device, when the connection to the electrical energy source is effective in situ, in the presence of body fluid, a closed electrical circuit is formed, with production of hydrogen at the cathode, the semi-permeable material having a cutoff threshold of between 50 and 500 Da.

As it was explained hereinabove, the semi-permeable material (for example a membrane) has a cutoff threshold which is compatible with the chemical species that can participate in the desired reactions. The cutoff threshold is more preferably sufficient to prevent the entry of chemical species or of excessive quantities of chemical species that can disturb the operation of the device. This makes it possible to prevent molecules of a molecular mass from exceeding the cutoff threshold and able on the one hand to electrochemically react on the surface of the electrodes, on the other hand to be deposited thereon and in time prevent the effective operation thereof, arrive in contact with the electrodes. A cutoff threshold of about 1000 or about 2000 Da (g/mole) can be considered.

In a first embodiment, the electrodes are separated from the external environment by a semi-permeable material having a cutoff threshold of between about 50 and about 500 Da, in particular between about 50 and about 200 Da, more preferably of about 150, 100, 90, 80, 70, 60, or 50 Da. This device is in particular intended to induce the electrolysis of water and produce $H_2$ and $O_2$. Note that this device can be used in practice for the local production and use of $H_2$, $O_2$ or both molecules.

In this embodiment, the electrodes are individually and/or collectively separated from the body medium by the semi-permeable material. "Individually separated" means that each electrode is separated from the external environment by the semi-permeable material. This can be carried out for example by surrounding the electrode with a covering or a membrane. This can also be carried out by disposing the electrode in a device including a compartment for each electrode, with an element made of semi-permeable material between each compartment and the external environment. "Collectively separated" means that the two electrodes are separated from the external environment by the semi-permeable material, which can be carried out for example by surrounding the two electrodes by a membrane, or by disposing the electrodes in a device including a compartment for the two electrodes, with an element made of semi-permeable material between the compartment and the external environment. Thus, the semi-permeable material that separates the electrodes from the body medium can be constituted by a semi-permeable membrane that surrounds the two electrodes, or by a semi-permeable membrane that surrounds each electrode.

The operation in situ of the device is supplemented by the role of the electrolyte which makes it possible to close the electrical circuit. This electrolyte is supplied by the body medium in which the device is implanted. This electrolyte contains the cations required for this role, namely in particular $Na^+$, $K^+$, $Ca^{2+}$, as well as the anions, substantially $Cl^-$ and $HCO_{3-}$.

In a second embodiment, the electrodes are separated from the external environment by a semi-permeable membrane having a cutoff threshold of between about 200 and about 2000 Da, in particular between about 200 and about 500 Da, in particular between about 200 and about 300, more preferably about 500, 400, 300 or 200 Da. The anode contains or carries an enzyme able to catalyse the oxidation of a carbohydrate at the anode. This device is in particular intended to induce the oxidation of a carbohydrate, in particular glucose, and produce $H_2$. Alternatively, only the anode is associated with such a semi-permeable membrane, while the cathode is associated with a semi-permeable membrane of the preceding type (lower cutoff threshold, in particular between about 50 and about 150 Da).

In this embodiment, the electrodes are more preferably separated from one another by the semi-permeable material, having in particular the low cutoff threshold as defined hereinabove, in particular between about 50 and about 150 Da, or by a proton exchange membrane. Furthermore, the electrodes are separated from the external environment by the semi-permeable material, which can be carried out for example by surrounding the electrode or the two electrodes at the same time by a covering or a semi-permeable membrane, or by disposing the electrode in a device including a compartment for each electrode, with an element made from a semi-permeable material between each compartment and the external environment. Thus, the semi-permeable material that separates the electrodes from the body medium can be constituted by a semi-permeable membrane that surrounds the two electrodes, or by a semi-permeable membrane that surrounds each electrode.

The operation in situ of the device is supplemented by the role of the electrolyte which makes it possible to close the electrical circuit. This electrolyte is supplied by the body medium in which the device is implanted. This electrolyte contains the cations required for this role, namely in particular $Na^+$, $K^+$, $Ca^{2+}$, as well as the anions, substantially $Cl^-$ and $HCO_{3-}$.

A proton-exchanging membrane (which can also be a rigid wall) or polymer electrolyte membrane (PEM) is a semi-permeable membrane manufactured from ionomers allowing for proton conduction while still being impermeable to gases such as dioxygen or dihydrogen: the protons pass through while the gases are stopped. This particularity is exploited in MEAs (Membrane Electrode Assemblies) of PEM fuel cells and PEM electrolysers. PEMs are manufactured from pure polymer membranes or composite membranes where the materials form a polymer matrix. One of the most widely used materials is Nafion, a fluorinated polymer produced by DuPont.

The device can include or be formed from a container wherein the electrodes are enclosed, the semi-permeable material that separates the electrodes from the body medium able to constitute a portion of said container. The container can include a single compartment or two compartments, as explained hereinabove. The container can be flexible, rigid or semi-rigid (at least one flexible portion and at least one rigid portion). The flexible form can be obtained through the use of the semi-permeable membrane for the manufacture thereof. The rigid form can be obtained through the use of a rigid material, for example polymer or composite, semi-permeable or the association of an impermeable rigid material and of a semi-permeable rigid material, made of polymer or composite for example. The semi-rigid form can be obtained through the use of a rigid material, for example polymer or composite, impermeable and a semi-permeable flexible membrane. An impermeable flexible material can be associated with a permeable flexible or rigid material.

As impermeable material, any biocompatible material can be used, for example glass, glass covered with parylene, elastomer, etc.

As semi-permeable rigid material, in particular a sintered ceramic or a sintered glass can be used.

In another embodiment, the semi-permeable material that separates the electrodes from the body medium can consist of a three-dimensional porous matrix, in at least one block, containing the two electrodes.

In another embodiment, the semi-permeable material can be surrounded by a biocompatible surface layer and with anti-biofouling property, also in semi-permeable material for separation with the body medium, or the semi-permeable material can have an anti-biofouling property.

The semi-permeable material can be polyvinyl alcohol (PVA)

As a flexible material of the semi-permeable membrane or electrode covering type, natural biocompatible membranes (for example chitosan—cross-linked for example with genepin in order to become non-biodegradable in physiological conditions—or cellulose or cellulose acetate) or synthetic (for example polyurethane, Nafion®, PVA, . . . ) can be used.

Said device has dimensions suited to the site of implantation, in particular to the space available. It can in particular have dimensions that represent a total volume less than or equal to about 12 ml, preferably at about 10, 9, 8, 7, 6, 5, 4, 3, 2, 1, 0.5 or 0.3 ml (it can be of any shape, in particular parallelepiped, cylindrical or in the shape of a disc). These dimensions extend with the source of energy when it is integrated, or without the source of energy when the latter is offset.

The electrodes are separated from one another in such a way as to allow for the operation of the device. The distance between the electrodes is defined by the value of the current of the water electrolysis. Indeed, for example at the cathode, the proton reduction creates a depletion layer of which the thickness depends on the value of the reduction current. In any case, the distance between electrodes has to be greater than the thickness of the depletion layer. Generally, the distance that separates them can be comprised between about 0.1 mm and about 1 cm, in particular between about 0.2 and about 7 mm, preferably between about 0.5 and about 5 mm. To illustrate this, this separation distance can be applied between two massive electrodes (3D) disposed in parallel, or between two 2D electrodes supported by two parallel supports or it can be the separation distance between two 2D electrodes disposed on the same support.

The composition of the electrodes is adapted according to the function of each one of them. They can be of the same material or of two different materials. They can be made from, or comprise: carbon, preferably graphite, carbon nanotubes, graphene, active charcoal; this carbon, preferably graphite, carbon nanotubes, graphene, active charcoal, can be doped, in particular with platinum, iron or gold; they can be made from platinum; gold, or doped diamond, in particular at least the anode can be made of gold, or gold doped. For example, in the case of the electrolysis of water, with a gold electrode, at a potential less than 1.2 V, no formation of dichloride is observed.

In the embodiment wherein a carbohydrate is used at the anode, the latter contains or carries an enzyme that is able to catalyse the oxidation of this carbohydrate or sugar. In the example of glucose, the enzyme can be glucose oxidase and/or glucose dehydrogenase. In this mode, redox mediators or cofactors can be added to the anode. These mediators and cofactors play the role of electron acceptors for the enzyme during the oxidation of the glucose. In particular, a catalase can be used as a second catalyst in the case of glucose dehydrogenase.

In this embodiment, the anode can be in particular formed from an agglomerate comprising a conductor material, in particular with a carbon base as described hereinabove (for example graphite, carbon nanotubes), a compound useful for the function of the electrode considered, such as an enzyme (for example glucose oxidase and/or glucose dehydrogenase) and another component used as a binder, in particular a polyoside, such as chitosan (preferably modified to stabilise it, for example by adding genepin), or a polymer, such as a polyvinyl alcohol polymer (PVA) or a polyacrylic acid polymer (PAA). These electrodes can be for example produced by compression.

An example of the production of electrodes of this type is described in FR 2 958 801. According to an embodiment of the present invention, the enzyme at the anode is selected from the group comprising glucose-oxidase and glucose dehydrogenase. The conductor material is for example graphite or a conductor polymer. The electrode can be formed by compression of a mixture in a solution comprising the conductor associated with the enzyme. The electrode body is preferably formed by compression of graphite mixed with the enzyme. A powder of a conductive polymer can also be used such as polyaniline, polypropylene, polyvinylidene fluoride. The resulting pastes (for example graphite-enzyme) can be compressed at a sufficient pressure, for example of about 10,000 kg/cm$^2$.

Another example of electrode production that has an improved service life is described in FR 14/52534. The electrode is formed from chitosan, the enzyme and the conductor. This electrode can be produced by compression, as is taught in this document. The conductor can advantageously be constituted of carbon nanotubes, for example SWCNT (Single-Walled Nanotubes) or MWCNT (Multi-Walled Carbon NanoTubes).

The anode comprising glucose oxidase is an embodiment of the invention, intended for the use of glucose. It is also possible to add to this enzyme a molecule, called redox mediator, capable providing an electron transfer between the glucose oxidase and the surface of the electrode. Therefore, in an alternative of this embodiment, these anodes comprising glucose oxidase also comprise a mediator. This can in particular be ferrocene, osmium complex, methylene blue, and/or a quinone derivative. This mediator can be immobilised on the surface of the electrode in particular be added to the initial mixture, in particular by pre-compression. The immobilisation of the mediator and optionally of the enzyme can be done via covalent grafting on the surface of the electrode, by physical adsorption on the surface of the electrode, by encapsulation or trapping in a polymer matrix (Chitosan, PVA, Nafion, etc).

In another embodiment for the use of glucose, glucose dehydrogenase is used. Preferably, the anodes comprising glucose dehydrogenase further comprise a cofactor intended to play the role of an electron acceptor. This cofactor can be in particular be: NAD (nicotinamide adenine dinucleotide), NADP (nicotinamide adenine dinucleotide phosphate), PQD (pyrroloquinoline quinone), and/or FAD (flavin adenine dinucleotide). In an embodiment, the glucose dehydrogenase oxidises the glucose and reduces the cofactor of which the reduced form oxidises on the surface of the electrode. In the NAD+ or NADP+, the surface can be modified or not by a polymer which makes it possible to facilitate the oxidation of the cofactor. This polymer can be poly(methylene blue), poly(methylene green) or poly(neutral red), electrochemically or chemically deposited on the surface of the anode.

The electrodes can have a 2D geometry. These 2D electrodes can be manufactured by deposition of an electrode-forming material on a support or two supports. A single support can be used for the two electrodes with the condition that the support is not electrically conductive. As a support, mention can be made of a thin sheet of graphite, platinum or gold, a thin sheet of "Gas diffusion Layer", a sheet of paper, glass, silicon. The deposition can be: physical deposition (PVD, cathodic evaporation, lithography, plasma deposition, etc.), electrochemical, printing, spray, or mechanical compression, chemical deposition (CVD, sol-gel, etc.)

The electrodes can have a 3D geometry. They can be formed conventionally, preferably by compression (for example as described hereinabove), stereolithography, 3D printing.

The electrodes, in particular when they are made of metal, for example gold or platinum, can also be strips, for example a few centimetres long, a few millimetres wide, a few tens or hundreds of microns thick, or bare wires (3D form category).

The source of energy can be a battery, preferably a high-density energy battery, for example a Lithium battery.

The source of energy can be a biobattery able to produce electricity by consuming chemical species that are naturally present in the human or animal organism, such as: glucose, carbohydrates, lipids, proteins.

The biobattery can be an enzymatic biobattery (for example operating with glucose oxidase, see for example FR 2 958 801, glucose dehydrogenase (Yonghai Song et al., ChemElectroChem 2017, 4, 1457-1462), laccase, bilirubin oxidase); a biomimetic biobattery, see for example WO2009003936.

The source of energy can be a device for recovering mechanical energy, exploiting for example the piezoelectric effect (WO2017048906, Geon-Tae Hwang et al., Advanced Materials Volume 26, Issue 28, Jul. 23, 2014, pages 4880-4887.

The source of energy is preferably capable of producing a voltage of at least about 1.3 V and a power of at least about 5 microWatts. To produce this energy, as shall be seen hereinafter, a voltage booster can be added to the source of energy. Unless mentioned otherwise in what follows, when mention is made of what provides the source of energy, this means that it provides alone or, in association with the voltage booster. For example, the power will be comprised between about 5 microWatts and about 10 milliWatts, in particular between about 250 microWatts and about 1 milliWatts. Examples of power are about 5 microWatts, about 250 microWatts, about 1 milliWatts, about 10 milliWatts. For example the voltage is comprised between about 1.3 V and about 3 V, in particular between about 1.3 V and about 1.5 V.

In an alternative, the source of energy is a battery that can be recharged via transcutaneous energy transfer, for example according to U.S. Pat. No. 8,620,447.

The device can also comprise a voltage booster, able to transform the voltage produced into a higher voltage. For example, in the case of a biobattery, such as a glucose biobattery, producing a voltage less than 1 or 1.3 V, the voltage booster makes it possible to obtain a higher voltage, for example greater than about 1.3 V, which makes it possible to provide the desired reaction at the anode, such as water hydrolysis.

In an improved embodiment, the device comprises an element for controlling the opening and the closing of the physical electrical circuit. This can be a switch, in particular placed on a conductor connected to the source of energy. It is in particular controlled by a remote control and/or a calculator, making it possible to control this element or switch in a one-off or programmed manner.

The device according to the invention has the advantage of insulating the electrodes from the surrounding tissues. The electric field is focused between the two electrodes and the vicinity thereof, but remains insulated from the tissues in order to limit the electrical current that can touch them or pass through them.

The invention also has for object a method for the production in vivo (in situ) of hydrogen and/or oxygen inside the body of a human or animal. In this method a device according to the invention is made to operate, which was put into place. This method can also comprise putting in place of the device in the body. This can in particular be done by a surgical act, suited to the implantation site and to the dimensions of the device. This method can provide the implantation of several of these devices, at the desired locations, and/or of devices that group several pairs of electrodes together. When there are several devices or pairs of electrodes therein, the source of energy can be specific or shared. The method can also comprise the act of electrically connecting a device to a remote source of energy. The method can also provide controlling the closing and the opening of the circuit by the means provided for this purpose.

"Animal" in terms of the invention means in particular large animals, sport animals (in particular horse), and pets such as dogs and cats.

BRIEF INTRODUCTION OF THE DRAWINGS

The invention shall now be described in more detail using embodiments described by way of non-limiting examples and in reference to the accompanying drawing, wherein.

DETAILED DESCRIPTION

Figure 1:
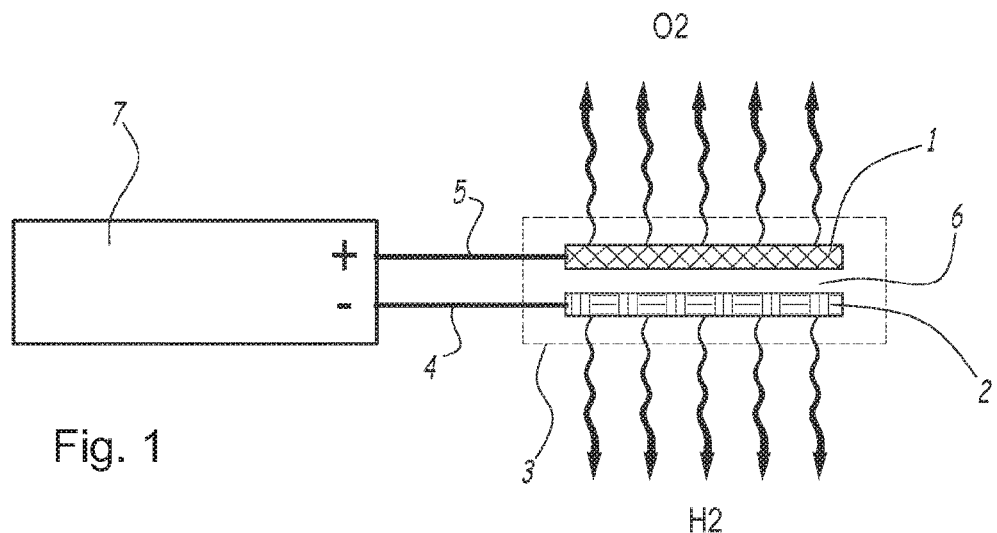
FIG. 1 is a diagram of a first device for the hydrolysis of water.

Example 1: Device for the Hydrolysis of Water

The device is formed from an anode 1 and from a cathode 2, placed inside a semi-permeable membrane 3, insulated conductor wires, namely conductor 4 connecting the cathode 2 to the pole (−) of a source of energy, and conductor 5 connecting the cathode 2 to the pole (+) of the source of energy. The energy source is a Lithium battery 7 (Lithium-CFx), delivering between 3.2 V and 2.5 V, and connected to a circuit making it possible circulate between anode and cathode a current of 8 microAmperes under 1.3 V. The semi-permeable membrane has a cutoff threshold of 100 Da. The electrodes are platinum strips, they are disposed in parallel and separated by a space 6 of 3 mm.

In operation, water and electrolytes present in the medium penetrate inside the space created by the semi-permeable membrane. Under the effect of the electric current delivered by the Lithium battery, the water is electrolysed, leading to the release of hydrogen at the cathode and of oxygen at the anode.

Example 2: Device for the Hydrolysis of Water

This device differs from the one of example 1 by the fact that the membrane 3 is replaced with two semi-permeable membranes 8 and 9, surrounding the anode, respectively the cathode. The semi-permeable membranes have a cutoff threshold of 150 Da.

Example 3: Device for Producing Hydrogen Using Glucose

The device is formed from an anode 10 and from a cathode 12, each placed inside a semi-permeable membrane 11, respectively 13, insulated conductor wires, namely conductor 14 connecting the cathode 12 to the pole (−) of a source of energy, and conductor 15 connecting the anode 10 to the pole (+) of the source of energy. The source of energy is a Lithium battery 16, delivering between 3.2 V and 2.5 V, and connected to a circuit making it possible circulate between anode and cathode a current of 1 milliAmpere under 0.3 V. The cathode is an electrode 3D made of carbon nanotubes, laccase, chitosan and genepin, the anode is an electrode 3D formed from carbon nanotubes, glucose oxidase, chitosan and genepin, according to the teaching of FR 3 019 384. The membrane 11 has a cutoff threshold of 500 and the membrane 13 has a cutoff threshold of 200.

Alternatively, the membrane 11 has a cutoff threshold of 200 and the membrane 13 has a cutoff threshold of 100. In an alternative not shown, a Nafion® membrane is provided between the two electrodes.

In operation,
at the anode:
the glucose passes through the semi-permeable membrane the glucose oxidase transforms it into gluconate+2 H$^+$+2 e$^-$. The electrons are captured by the anode. The gluconate passes back through the membrane, as well as the protons.

at the cathode:

2 electrons are combined with two protons to give H$_2$.

According to the invention, when glucose is used, it is possible to provide catalase to retransform H$_2$O$_2$ into H$_2$O and ½ O$_2$, in which case the presence of O$_2$ at the anode would allow for a parasite reaction with the glucose leading to the formation of H$_2$O$_2$.

Another alternative consists, with or without the presence of catalase, of applying a high voltage at the anode (>0.6V) in order to oxidise H$_2$O$_2$.

Further alternatively, the glucose oxidase is replaced with the glucose dehydrogenase. The anode then includes this enzyme and, in addition, a cofactor.

Example 4: Hydrolysis of Water, Lithium Battery

Many clinical studies demonstrate a beneficial effect of the ingestion of water saturated with H$_2$, corresponding to a minimum intake of about 240 micromoles/24 h. The continuous production of H$_2$ by a device implanted according to the invention makes it possible to obtain an average concentration in the extra-cellular and intra-cellular fluid greater than the average concentration obtained by oral ingestion, with significantly lower initial quantities.

Figure 2:
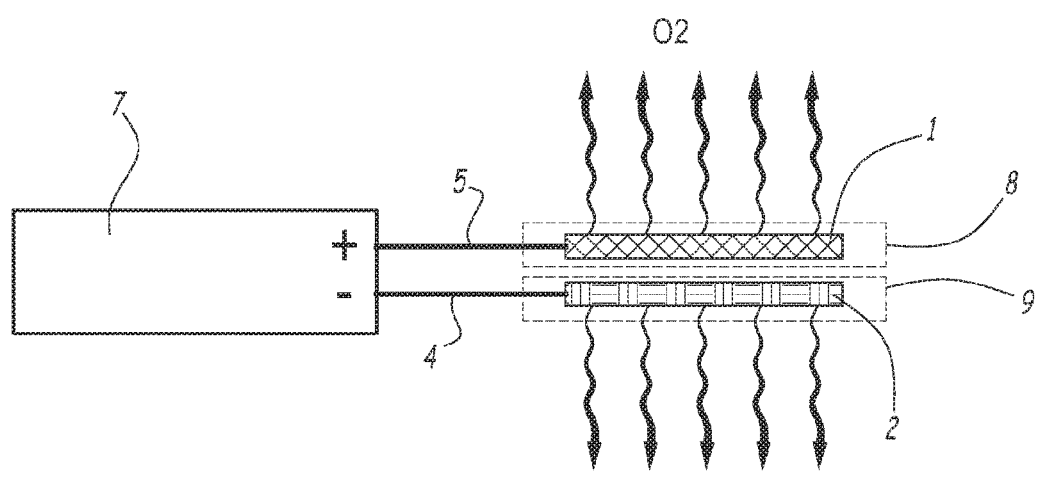
FIG. 2 is a diagram of a second device for the hydrolysis of water.

In this example, the production of 240 micromoles/24 h of hydrogen by the devices of the diagrams in FIGS. 1 and 2 is described.

By way of example, the device is implanted in patients carrying an Alzheimer's disease and carriers of the apolipoprotein genotype E4 (APOE4) (cf. https://www.ncbi.nlm-.nih.ciov/pubmed/29110615, this study showing an interest of the ingestion of 300 mL per day of hydrogen water).

In this example, the source of energy is a Lithium-CFx battery of the type of those used in wireless pacemakers, that operate under a voltage comprised between 3.2 V and 2.5 V.

|  | NanoStim ® | Medtronic |
|---|---|---|
| Capsule dimensions | Length 41.4 mm, diameter 6 mm, volume 1-1.2 cc | Length 25.9 mm, diameter 6.7 mm, volume 0.8-1 cc |
| Masse capsule | 2 g | 1.75 g |
| Battery capacity | 220 mAh | 120 mAh |
| Battery dimensions | length 25 mm, diameter 6 mm | length 11 mm, diameter 6.7 mm |

The power embarked in the Nanostim battery is therefore 2376 J, in a volume of 760 microL, which is about 3 J/microL. However, to produce H$_2$ via water hydrolysis, with a yield of 70%, about 0.4 J/(micromole of H$_2$) can be provided. Therefore, in order to produce 240 micromoles of H$_2$ per 24 h, a battery with a volume of about 32 microL can be used. A 12.8 mL battery then makes it possible to embark the required power for 400 days, which is more than one year.

The electrodes will be constituted of platinum strips 0.1 mm thick, 4 cm long, 2.5 cm wide, placed in a semi-permeable membrane.

The entire device can be positioned, just like a conventional pacemaker, under the collarbone.

This example describes the formation of H$_2$. But of course, it also applies to the generation of O$_2$, taking into account the fact that twice the amount of energy is required to produce one mole of O$_2$ than one mole of H$_2$.

Example 5

Figure 3:
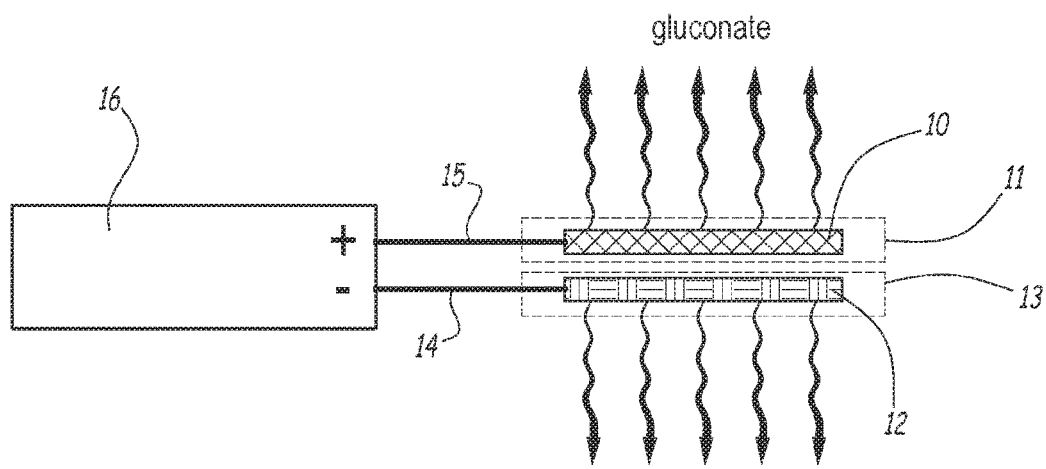
FIG. 3 is a diagram of a first device using the glucose.

In this example, the anode of the device of FIG. 3 includes a glucose oxidase and a mediator (ferrocene, osmium complex, methylene blue, or quinone derivative). A difference in potential of 0.3 V is then sufficient to oxidise the glucose at the anode and to reduce the proton at the cathode. The power needed is therefore divided by 1.3/0.3=4.33. The dimension of the battery is then reduced to 12.8/4.33=2.9 mL. Alternatively, by retaining a dimension of 12 mL for the battery, a service life of the device of 1,732 days is obtained, which is nearly 5 years.

This device can be used in the application of the preceding example, for the production of hydrogen.

Example 6

With respect to example 5, the battery that supplies the 0.3 V is a glucose biobattery, according to the teachings of patents such as FR 3 019 384 and FR 2 958 801.

Example 7: Implantation Sites of the Device

According to the needs, it is possible to implant 1 or several devices according to the invention. The choice is made in particular with regards to the extent of the area to be treated, the need for hydrogen and/or oxygen of this area, the capacity of the implantation site to receive in terms of volume one or several devices, the power of each device in terms of production and the diffusion and distribution capacity of the hydrogen and/or of the oxygen in this site/this area.

As implantation sites, mention can be made of under the skin, in the or in the vicinity of the brain (in particular inside the brain ventricles), in the intestine, the heart.

Under the skin:
subcutaneous: volume up to 20 mL
intra-muscular: volume up to 125 microL
in the intestine: it is possible to consider several devices threaded one after the other on a line which is itself attached in the stomach, according to the teachings of patent FR1552927, each one of a diameter of 6 mm and of a length of 5 cm, which is 1.4 mL. For example, from 10 to 20 segments can be considered
in the heart: typical size of the "lead less pacemaker" stimulators=6 mm diameter×25 mm long, which is 700 microL Example 8

Figure 4:
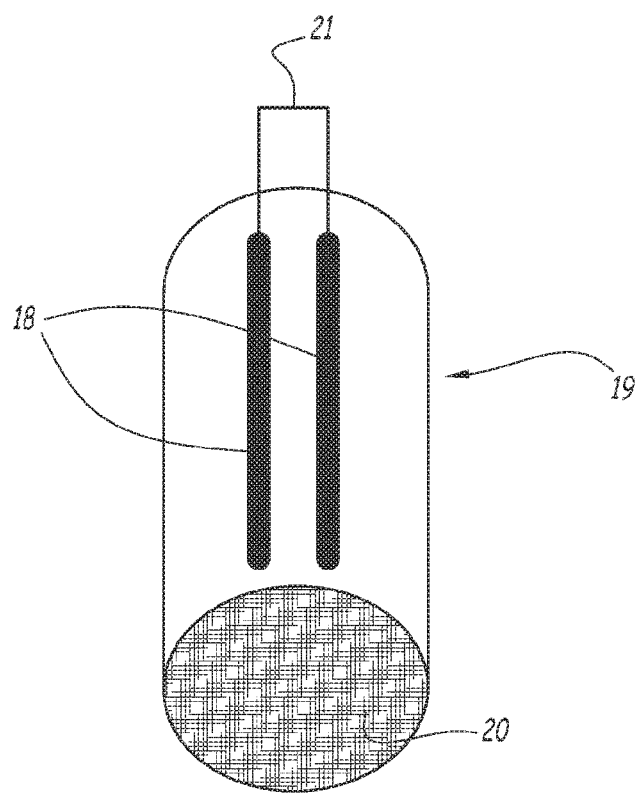
FIG. 4 is a diagram of a rigid device.
Figure 5:
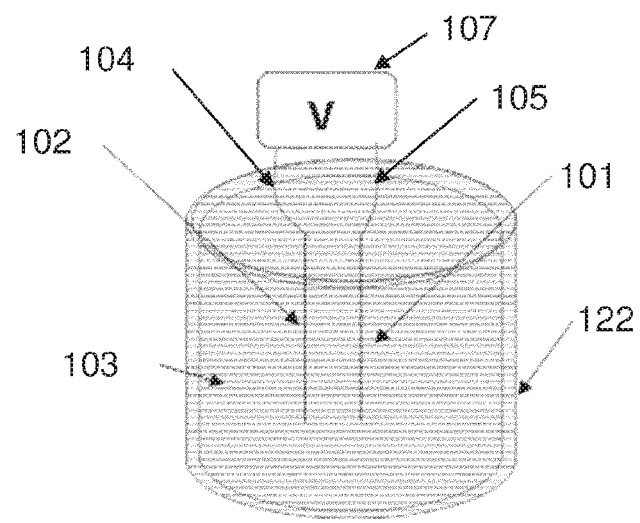
FIG. 5 is a diagram of a third device for the hydrolysis of water.
Figure 6:
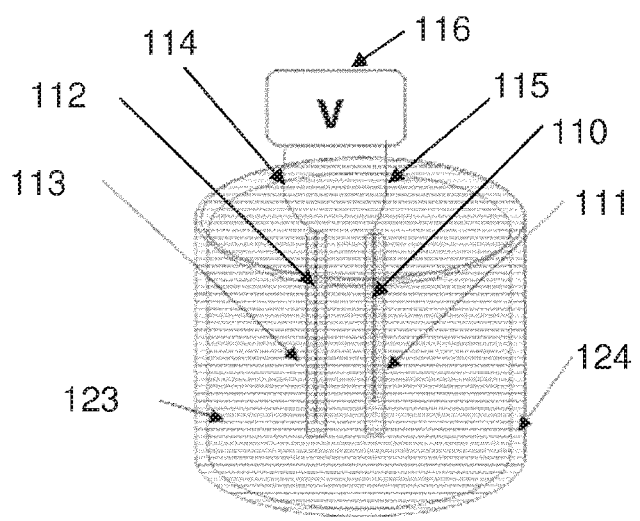
FIG. 6 is a diagram of a second device using the glucose.

FIG. 4 diagrammatically shows a device in the form of a cylindrical container, of which the body 19 is made of glass covered with parylene, or could be entirely of parylene. This body has an opening at one of the tops of the cylinder, which is closed by a disc 20 made of semi-permeable composite material. The two electrodes 18 and a simplified electrical circuit 21 are shown, whereas the source of energy is not shown Example 9: Dispositive for the Electrolysis of Water in a Porous Matrix The device is formed from an anode 101 and from a cathode 102 which are placed in a porous matrix 103.

Conductor wires 104 and 105 respectively connect the cathode 102 to the pole (−) and the anode 101 to the pole (+) of the source of energy 107.

The porous matrix 103 is formed from a semi-permeable material, has a cutoff threshold from 50 to 100 Da and is covered with a biocompatible surface layer 122 and has anti-biofouling properties. This surface layer 122 is also semi-permeable and has a cutoff threshold from 50 to 100 Da.

The porous matrix 103 makes it possible to prevent any cell growth inside the latter and an electrical current from circulating in the living tissues surrounding the device.

In the electrolysis of the water, the ions $H^+$ are reduced at the cathode in order to produce dihydrogen and the water is oxidised at the anode with production of dioxygen.

It can be noted that the case is also considered where the matrix 103 itself has anti-biofouling properties, in which case the layer 122 is not used.

Example 10: Device with Enzymatic Catalysis in a Porous Matrix

The device is formed from an anode 110 and from a cathode 112 which are each placed in a semi-permeable membrane respectively 111 and 113. Conductor wires 114 and 115 respectively connect the cathode 112 to the pole (−) and the anode 110 to the pole (+) of the source of energy 116.

The anode 110 and the cathode 112 each covered by a semi-permeable membrane, respectively 111 and 113 are placed in a porous matrix 123. The porous matrix is covered with a biocompatible surface layer 124 and with anti-biofouling properties.

The anode 110 has an enzyme that makes it possible to conduct the oxidation of the glucose into gluconate.

So that the glucose can reach the anode 110, the surface layer 124, the porous matrix 123 as well as the semi-permeable membrane 111 all have a cutoff threshold greater than 200 Da.

The cutoff threshold of the semi-permeable membrane 113 which is disposed on the cathode 112 is from 50 to 100 Da.

It is also possible to not cover the anode 110 and the cathode 112, in that the matrix 123 already provides the selectivity.

It can be noted that the case is also considered where the matrix 123 itself has anti-biofouling properties, in which case the layer 124 is not used.

The invention claimed is:

1. A device intended to be implanted in a human or animal body, in order to produce hydrogen in situ from molecules present in a body medium in which the device is implanted, this device comprising two electrodes: an anode and a cathode, the anode is electrically connected to a pole of an electrical energy source and the cathode is electrically connected to an other pole of the electrical energy source, and comprising a semi-permeable material separating the electrodes from the body medium, and wherein, when the connection to the electrical energy source is effective in situ, in the presence of body fluid, a closed electrical circuit is formed, with production of hydrogen at the cathode, the semi-permeable material having a cutoff threshold of between 50 and 500 Da.

2. The device according to claim 1, wherein the semi-permeable material has a cutoff threshold between 50 and 500 Da, and the device is intended to induce electrolysis of water, with production of dioxygen at the anode.

3. The device according to claim 2, wherein the electrodes are individually or collectively separated from the body medium by the semi-permeable material.

4. The device according to claim 1, wherein the semi-permeable material has a cutoff threshold between 200 and 500 Da, and wherein the anode contains or carries an enzyme able to catalyse the oxidation of a carbohydrate at the anode.

5. The device according to claim 4, wherein the electrodes are individually and/or collectively separated from the body medium by the semi-permeable material and wherein the anode and cathode are separated one from the other by a semi-permeable membrane or by a proton exchange membrane.

6. The device according to claim 1, wherein the semi-permeable material that separates the electrodes from the body medium is formed by a semi-permeable membrane that surrounds the two electrodes, or by a semi-permeable membrane that surrounds each electrode.

7. The device according to claim 1, wherein the semi-permeable material that separates the electrodes from the body medium forms a portion of a container that encloses the electrodes.

8. The device according to claim 1, wherein the semi-permeable material that separates the electrodes from the body medium consists of a three-dimensional porous matrix, in at least one block, containing the two electrodes.

9. The device according to claim 5, wherein the semi-permeable material is surrounded by a biocompatible surface layer and with anti-biofouling property, also in semi-permeable material for separation with the body medium, or the semi-permeable material has an anti-biofouling property.

10. The device according to claim 1, wherein the semi-permeable material is polyvinyl alcohol (PVA).

11. The device according to claim 1, wherein the electrodes are made of or comprise: carbon; platinum; gold.

12. The device according to claim 1, wherein the anode contains or carries an enzyme able to catalyse the oxidation of the glucose at the anode, the enzyme being chosen from among glucose oxidase and glucose dehydrogenase, and a catalase able to be used as a second catalyst when the enzyme is glucose dehydrogenase.

13. The device according to claim 1, wherein the electrical energy source is one of a battery; a biobattery able to produce electricity by consuming chemical species that are naturally present in a human or animal organism; a mechanical device that recovers piezoelectric energy.

14. The device according to claim 1, wherein said device has dimensions that represent a volume less than or equal to 12 ml.

15. The device according to claim 1, wherein the electrical energy source produces a voltage of at least about 1.3 V and a power of at least about 5 microWatts.

16. The device according to claim 1, wherein the anode and cathode are separated by a distance between about 0.1 mm and about 1 cm.

17. A method for in vivo production of hydrogen and/or oxygen inside a human or animal body, comprising
an implantation of at least one device according to claim 1 in the human or animal body,
an operation of the device to produce hydrogen and/or oxygen inside in the human or animal body.

18. The method according to claim 17, further comprising electrically connecting the device to a remote electrical energy source.

19. The method according to claim 17, wherein the operation of the device comprises controlling closing and opening of the electrical circuit by an element for controlling the opening and the closing of the electrical circuit.

* * * * *